(12) United States Patent
Norikane et al.

(10) Patent No.: US 10,037,714 B2
(45) Date of Patent: Jul. 31, 2018

(54) HYDROGEL LIQUID PRECURSOR, LIQUID SET FOR THREE-DIMENSIONAL MODELING, HYDROGEL MODELING OBJECT, AND METHOD OF MANUFACTURING THREE-DIMENSIONAL OBJECT

(71) Applicants: Yoshihiro Norikane, Kanagawa (JP); Hiroshi Iwata, Kanagawa (JP)

(72) Inventors: Yoshihiro Norikane, Kanagawa (JP); Hiroshi Iwata, Kanagawa (JP)

(73) Assignee: Ricoh Company, Ltd., Tokyo (JP)

( * ) Notice: Subject to any disclaimer, the term of this patent is extended or adjusted under 35 U.S.C. 154(b) by 168 days.

(21) Appl. No.: 15/066,768

(22) Filed: Mar. 10, 2016

(65) Prior Publication Data

US 2016/0275818 A1 Sep. 22, 2016

(30) Foreign Application Priority Data

Mar. 20, 2015 (JP) ................. 2015-057312

(51) Int. Cl.

| | | |
|---|---|---|
| *G09B 23/30* | (2006.01) | |
| *C09D 133/14* | (2006.01) | |
| *C08K 5/5317* | (2006.01) | |
| *C08K 3/34* | (2006.01) | |
| *C08F 220/56* | (2006.01) | |
| *C08J 3/075* | (2006.01) | |
| *A61B 34/00* | (2016.01) | |
| *B29C 64/112* | (2017.01) | |
| *B33Y 10/00* | (2015.01) | |
| *B33Y 70/00* | (2015.01) | |
| *B33Y 80/00* | (2015.01) | |
| *B29L 31/00* | (2006.01) | |
| *B29L 31/40* | (2006.01) | |
| *B29K 105/00* | (2006.01) | |

(52) U.S. Cl.
CPC .............. *G09B 23/30* (2013.01); *A61B 34/00* (2016.02); *B29C 64/112* (2017.08); *C08F 220/56* (2013.01); *C08J 3/075* (2013.01); *C08K 3/34* (2013.01); *C08K 5/5317* (2013.01); *C09D 133/14* (2013.01); *B29K 2105/0002* (2013.01); *B29K 2105/0061* (2013.01); *B29K 2105/0094* (2013.01); *B29L 2031/40* (2013.01); *B29L 2031/7532* (2013.01); *B33Y 10/00* (2014.12); *B33Y 70/00* (2014.12); *B33Y 80/00* (2014.12)

(58) Field of Classification Search
CPC ....................................................... G09B 23/30
USPC ........................................................... 524/123
See application file for complete search history.

(56) References Cited

U.S. PATENT DOCUMENTS

| | | | | |
|---|---|---|---|---|
| 2004/0132869 | A1* | 7/2004 | Peppmoller | C05D 9/00 524/13 |
| 2014/0219973 | A1* | 8/2014 | Boyes | A61L 27/52 424/93.7 |

FOREIGN PATENT DOCUMENTS

| | | |
|---|---|---|
| JP | 2002-053629 A | 2/2002 |
| JP | 2002-053762 A | 2/2002 |
| JP | 2005-500407 A | 1/2005 |
| JP | 2009-046532 A | 3/2009 |
| JP | 2011-011934 A | 1/2011 |
| JP | 2015-136895 A | 7/2015 |
| JP | 2015-138192 A | 7/2015 |
| WO | WO2003/000621 A1 | 1/2003 |
| WO | WO2015/111366 A1 | 7/2015 |

OTHER PUBLICATIONS

U.S. Appl. No. 14/876,055, filed Oct. 6, 2015.

\* cited by examiner

*Primary Examiner* — Doris L Lee
(74) *Attorney, Agent, or Firm* — Oblon, McClelland, Maier & Neustadt, L.L.P.

(57) ABSTRACT

A hydrogel liquid precursor includes an inorganic mineral and a monomer, wherein the inorganic mineral accounts for 15 percent by mass or more of the hydrogel liquid precursor, wherein the hydrogel liquid precursor has an initial viscosity of 20 mPa·s or less at 25 degrees C., and wherein the hydrogel liquid precursor has a ratio of a two-week viscosity to the initial viscosity of from 0.90 to 1.10, the two-week viscosity representing a viscosity of the hydrogel liquid precursor at 25 degrees C. after being left at 50 degrees C. for two weeks.

8 Claims, 3 Drawing Sheets

HYDROGEL LIQUID PRECURSOR, LIQUID SET FOR THREE-DIMENSIONAL MODELING, HYDROGEL MODELING OBJECT, AND METHOD OF MANUFACTURING THREE-DIMENSIONAL OBJECT

CROSS-REFERENCE TO RELATED APPLICATIONS

This patent application is based on and claims priority pursuant to 35 U.S.C. § 119 to Japanese Patent Application No. 2015-057312 filed on Mar. 20, 2015, in the Japan Patent Office, the entire disclosure of which is hereby incorporated by reference herein.

BACKGROUND

Technical Field

The present invention relates to a hydrogel liquid precursor, a liquid set for three-dimensional modeling, a hydrogel modeling object using the liquid or the liquid set, and methods of manufacturing 3D objects using the liquid or the liquid set.

Background Art

Small lot production of a complex and fine object is increasingly demanded. Of these 3D objects, internal organ model for procedure practices for surgery are strongly demanded, reproducing softness to a degree that the model can be cut open by a surgical scalpel, bite and touch of the object extremely close to those of internal organs, and a true-to-life form of the internal organ of individual patients. Hydrogel is a good candidate as the model because softness and touch of such a hydrogel are close to those of real internal organs.

SUMMARY

According to the present invention, provided is an improved hydrogel liquid precursor including an inorganic mineral and a monomer, wherein the inorganic mineral accounts for 15 percent by mass or more of the hydrogel liquid precursor, wherein the hydrogel liquid precursor has an initial viscosity of 20 mPa·s or less at 25 degrees C., and wherein the hydrogel liquid precursor has a ratio of a two-week viscosity to the initial viscosity of from 0.90 to 1.10, the two-week viscosity representing a viscosity of the hydrogel liquid precursor at 25 degrees C. after being left at 50 degrees C. for two weeks.

BRIEF DESCRIPTION OF THE SEVERAL VIEWS OF THE DRAWINGS

Various other objects, features and attendant advantages of the present invention will be more fully appreciated as the same becomes better understood from the detailed description when considered in connection with the accompanying drawings in which like reference characters designate like corresponding parts throughout and wherein.

DETAILED DESCRIPTION

Figure 1:
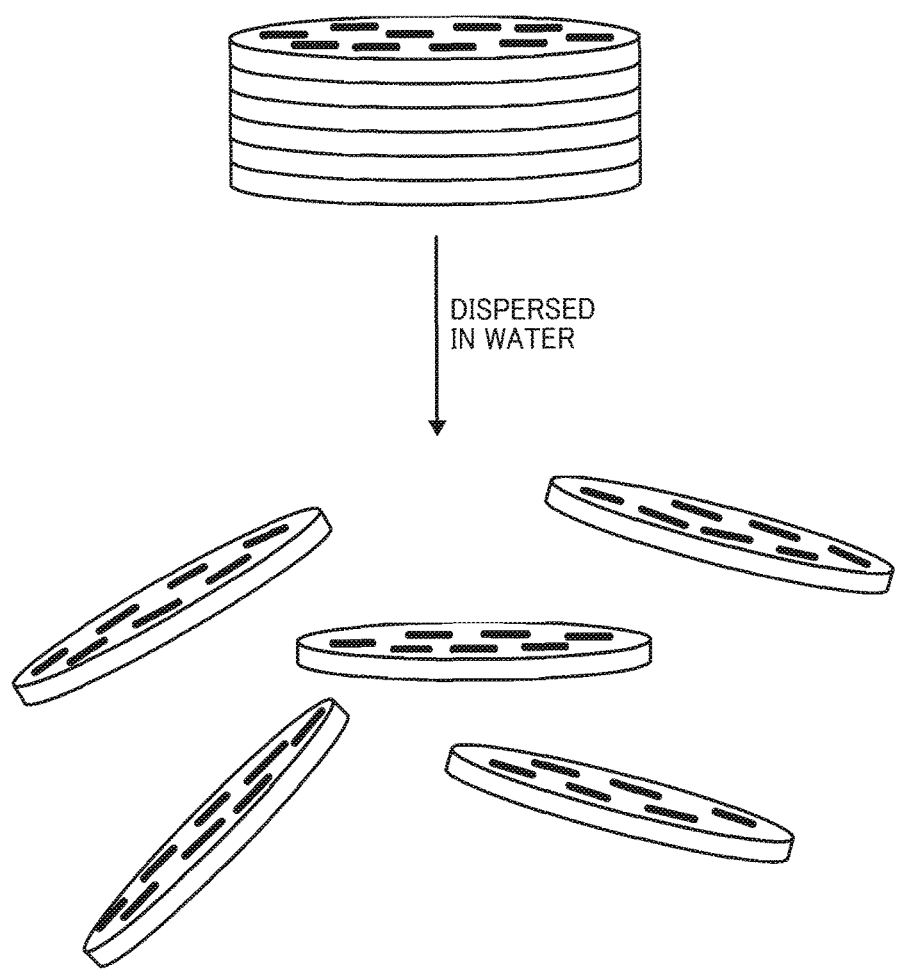
FIG. 1 is a schematic diagram illustrating an example of a laminate mineral and a state in which the laminate mineral is dispersed in water.

Internal organ model for procedure practices for surgery are strongly demanded, reproducing softness to a degree that the model can be cut open by a surgical scalpel, bite and touch of the object extremely close to those of internal organs, and a true-to-life form of the internal organ of individual patients. Hydrogel is a good candidate as the model because softness and touch of such a hydrogel are close to those of real internal organs. A specific example of the hydrogel contains water in the three-dimensional network structure formed by compounding a laminate mineral and a polymer.

However, such a hydrogel is relatively soft (i.e., modulus of elasticity is low) so that a relatively hard hydrogel (i.e., modulus of elasticity is high) is not obtained The present disclosure is to provide a hydrogel liquid precursor having a good storage property and suitable to manufacture a hydrogel modeling object having a complex inner structure including a modeling portion having a high modulus of elasticity shaped by a hydrogel modeling object having a high modulus of elasticity with a modeling portion having a low modulus of elasticity disposed at an arbitrary area.

Hydrogel Liquid Precursor

The hydrogel liquid precursor of the present disclosure includes an inorganic mineral and a monomer, preferably a phosphonic acid compound, and other optional components.

Inorganic Mineral

The inorganic mineral is contained to enhance the modulus of elasticity (80 percent compressive stress-strain or modulus of compressive elasticity) of a hydrogel modeling object.

The inorganic mineral has no specific limit and is suitably selected to a particular application. For example, laminate mineral is usable.

The laminate mineral includes crystal having a two-dimensional disk-like form having unit lattices in the crystal. Single layers of the laminate mineral are piled up as illustrated on the upper part of FIG. 1 and when the laminate mineral is dispersed in water, the mineral is separated into each signal layer having a disk-like form as illustrated on the lower part of FIG. 1.

The laminate mineral has no particular limit and, for example, water swellable laminate clay minerals are suitable.

Examples of such clay minerals are water swellable smectite and water swellable mica. Specific examples thereof include, but are not limited to, water swellable hectorite, water swellable montmorillonite, water swellable saponite, and water swellable synthesized mica. These can be used alone or in combination. Of these, water swellable hectorite is preferable to obtain hydrogel modeling objects having high elasticity.

Water swellable hectorite can be appropriately synthesized or is available on market. Specific examples of the synthesized hectorite (laponite XLG, manufactured by RockWood), SWN (manufactured by Coop Chemical Ltd.), and fluorinated hectorite SWF (manufactured Coop Chemical Ltd.). Of these, synthesized hectorite is preferable in terms of modulus of elasticity of a hydrogel modeling object.

"Water swellable" means that water molecules are inserted between layers of the inorganic mineral and the inorganic mineral is dispersed as illustrated in FIG. 1.

Since the modulus of elasticity and hardness of a hydrogel modeling object are set to a value or higher, the content of the inorganic mineral of a hydrogel modeling object accounts for 15 percent by mass or more of the total content of the hydrogel liquid precursor. Also, in terms of viscosity (inkjet dischargeability) of the hydrogel liquid precursor and dispersibility of the inorganic mineral in the hydrogel liquid precursor, the content of the inorganic mineral preferably accounts for 15 percent by mass to 40 percent by mass and more preferably 15 percent by mass to 25 percent by mass.

Monomer

The monomer is not particularly limited as long as the monomer is capable of cross-linking with the inorganic mineral. For example, water soluble monomers are preferable.

Water-solubility of the water soluble monomer means, for example, when 1 g of a homopolymer of the water soluble monomer is mixed and stirred in 100 g of water at 30 degrees C., 90 percent by mass or more of the homopolymer is dissolved therein.

The monomer is a compound having at least one unsaturated carbon-carbon bond and includes, for example, a mono-functional monomer and a multi-functional monomer. Furthermore, the multi-functional monomer includes a bi-functional monomer and a tri- or higher functional monomer.

As the monomer, an active energy ray polymerization type monomer is preferable in terms of modeling property of the hydrogel modeling object.

The mono-functional monomer is a compound having a single unsaturated carbon-carbon bond and specific examples thereof includes, for example, acrylamides, N-substituted acrylamide derivatives, N,N-di-substituted acrylamide derivatives, N-substituted methacrylamide derivatives, N,N-di-substituted methacrylamide derivatives, and other mono-functional monomers. These can be used alone or in combination.

The N-substituted acrylamide derivatives, N,N-di-substituted acrylamide derivatives, N-substituted methacrylamide derivatives, and N,N-di-substituted methacrylamide derivatives include, for example, N,N-dimethyl acryl amide (DMAA) and N-isopropyl acryl amide.

Specific examples of the other mono-functional monomers includes, but are not limited to, 2-ethylhexyl(meth) acrylate (EHA), 2-hydroxyethyl(meth)acrylate (HEA), 2-hydroxypropyl(meth)acrylate (HPA), acryloylmorpholine (ACMO), caprolactone-modified tetrahydrofurfuryl (meth) acrylate, isobonyl(meth)acrylate, 3-methoxybutyl(meth) acrylate, tetrahydrofurfuryl(meth)acrylate, lauryl(meth) acrylate, 2-phenoxyethyl(meth)acrylate, isodecyl(meth) acrylate, isooctyl(meth)acrylate, tridecyl(meth)acrylate, caprolactone(meth)acrylate, ethoxyfied nonylphenol(meth) acrylate, and urethane(meth)acrylate. These can be used alone or in combination.

Water soluble organic polymers having an amide group, an amino group, a hydroxyl group, a tetramethyl ammonium group, a silanol group, an epoxy group, etc. are obtained by polymerizing the mono-functional monomers mentioned above.

Water soluble organic polymers having an amide group, an amino group, a hydroxyl group, a tetramethyl ammonium group, a silanol group, an epoxy group, etc. are advantageous to maintain the strength of a hydrogel modeling object.

The content of the mono-functional monomer is not particularly limited but it is preferably from one percent by mass to 10 percent by mass and more preferably from 1 percent by mass to 5 percent by mass to the total content of the hydrogel liquid precursor to a particular application. When the content is in the range of from one percent by mass to 10 percent by mass, dispersion stability of the inorganic mineral in a hydrogel liquid precursor is maintained and drawing property of a hydrogel precursor object is enhanced. The drawing property means that when a hydrogel modeling object is drawn, the hydrogel modeling object is not fractured (broken) but extended.

Specific examples of the bi-functional monomers include, but are not limited to, tripropylene glycol di(meth)acrylate, triethylene glycol di(meth)acrylate, tetraethylene glycol di(meth)acrylate, polypropylene glycol di(meth)acrylate, neopentyl glycol hydroxy pivalic acid ester di(meth)acrylate (MANDA), hydroxypivalic acid neopentyl glycol ester di(meth)acrylate (HPNDA), 1,3-butanediol di(meth)acrylate (BGDA), 1,4-butanediol di(meth)acrylate (BUDA), 1,6-hexane diol di(meth)acrylate (HDDA), 1,9-nonane di(meth) acrylate, diethylene glycol di(meth)acrylate (DEGDA), neopentyl glycol di(meth)acrylate (NPGDA), tripropylene glycol di(meth)acrylate (TPGDA), caprolactone-modified hydroxy pivalic acid neopentyl glycol ester di(meth)acrylate, propoxinated neopentyl glycol di(meth)acrylate, ethoxy-modified bisphenol A di(meth)acrylate, polyethylene glycol 200 di(meth)acrylate, polyethylene glycol 400 di(meth)acrylate, and methylenebis acrylamide. These can be used alone or in combination.

Specific examples of the tri-functional monomers include, but are not limited to, trimethylol propane tri(meth)acrylate (TMPTA), pentaerythritol tri(meth)acrylate (PETA), tirallyl isocyanate, tris(2-hydroxyethyl)isocyanulate tri(meth)acrylate, ethoxyfied trimethylol propane tri(meth)acrylate, propoxyfied trimethylol propane tri(meth)acrylate, and propoxyfied glyceryl tri(meth)acrylate. These can be used alone or in combination.

Specific examples of the tri- or higher monomers include, but are not limited to, pentaerythritol tetra(meth)acrylate, ditrimethylol propanetetra(meth)acrylate, dipentaerythritol hydroxypenta(meth)acrylate, ethoxyfied pentaerythritol tetra (meth)acrylate, penta(meth)acrylate ester, and dipentaerythritol hexa(meth)acrylate (DPHA). These can be used alone or in combination.

The content of the multi-functional monomer is preferably from 0.001 percent by mass to 1 percent by mass and more preferably from 0.01 percent by weight to 0.5 percent by mass to the total content of the hydrogel liquid precursor. When the content is in the range of from 0.001 percent by mass to 1 percent by mass, it is possible to control the modulus of elasticity (80 percent compressive stress-strain or modulus of compressive elasticity) and hardness of the obtained hydrogel modeling object in a suitable range.

Phosphonic Acid Compound

The phosphonic acid compound is suitable to improve storage stability of the hydrogel liquid precursor.

The phosphonic acid compound includes, for example, phosphonic acid, salts of phosphonic acid, and intermediates thereof.

The phosphonic acid compound has no particular limit and the compound represented by the following Chemical formula 1 is preferable.

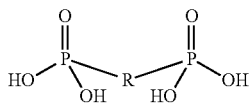

Chemical formula 1

In the Chemical formula 1, R represents a substituted or non-substituted divalent substitution group.

Specific examples of the divalent substitution group of R in the Chemical formula 1 include, but are not limited to, oxygen atom, sulfur atom, and alkyl groups. Of these, alkyl groups are preferable. When R is an alkyl group, the phosphoric acid compound is not hydrolyzed over time unlike pyrophosphoric acid where R is an oxygen atom. Therefore, the inorganic mineral is stably dispersed in the hydrogel liquid precursor, thereby improving the storage stability of the hydrogel liquid precursor.

The alkyl group of R in the Chemical formula 1 has not particular limit. In terms of adsorption to the inorganic mineral, —($R_1$)C($R_2$)— (where $R_1$ and $R_2$ each, independently represent substituted or non-substituted alkyl groups) is preferable.

$R_1$ and $R_2$ each, independently represent substituted or non-substituted alkyl groups. Specific examples thereof include, but are not limited to, methyl group and ethyl group. Specific examples of the substitution group of the alkyl group include, but are not limited to, hydroxy group, amino group, halogen atoms, and alkyl groups. Of these, —(OH)C($CH_3$)— is preferable in terms of storage stability.

Specific examples of the compound represented by the Chemical formula 1 include, but are not limited to, the compound (etidronic acid), alendronic acid, methylene diphosphonic acid, pyrophosphoric acid, phytic acid, nitrilotris methylene phosphonic acid (NTMP), and salts thereof. Of these, to obtain a hydrogel modeling object having a high modulus of elasticity, etidronic acid, alendronic acid, methylene diphosphonic acid, and salts thereof are preferable and etidronic acid and sodium salt of etidronic acid are more preferable.

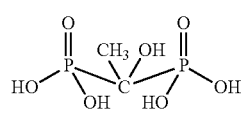

Chemical structure 1

The content of the phosphonic acid compound is preferably from 0.1 parts by mass to 10 parts by mass to 100 parts of the inorganic mineral in terms of improvement of dispersibility of the inorganic mineral. When the content is in the range of from 0.1 parts by mass to 10 parts by mass, adsorption to the inorganic mineral is sufficient, thereby strengthening the mutual action between the monomer and the inorganic mineral. As a result, the modulus of elasticity (80 percent compressive stress-strain or compressive modulus of elasticity) of a formed hydrogel modeling object tends to increase.

Solvent

The solvent has no particular limit. For example, solvents capable of dissolving the material of the hydrogel liquid precursor are suitable. Examples thereof are water and organic solvents. These can be used alone or in combination. Of these, water is preferable.

Water

As the water, deionized water, ultrafiltered water, reverse osmosis water, pure water such as distilled water, and ultra pure water can be used. It is suitable to dissolve or disperse other components such as organic solvents in the water to impart moisturizing property, antibiotic property, or electro-conductive property and adjust hardness.

The content of the water has no particular limit and can be selected to a particular application.

Organic Solvent

The organic solvent is preferably aqueous and for example, alcohols such as ethanol, ethers, and ketones are suitable.

The organic solvent has no particular limit. Specific examples of the organic solvent include, but are not limited to, 1,2,6-hexane triol, 1,2-butanediol, 1,2-hexane diol, 1,2-pentanediol, 1,3-dimethyl-2-imidazolidinone, 1,3-butanediol, 1,3-propane diol, 1,4-butanediol, 1,5-pentanediol, 1,6-hexane diol, 2,2-dimethyl-1,3-propane diol, 2,3-butanediol, 2,4-pentanediol, 2,5-hexane diol, 2-ethyl-1,3-hexane diol, 2-pyrolidone, 2-methyl-1,3-propane diol, 2-methyl-2,4-pentanediol, 3-methyl-1,3-butanediol, 3-methyl-1,3-hexane tanediol, N-methyl-2-pyrolidone, N-methyl pyrrolidinone, β-buthoxy-N,N-dimethylpropione amide, β-methoxy-N,N-dimethyl propione amide, γ-butylolactone, ε-caprolactam, ethylene glycol, ethylene glycol-n-butyl ether, ethylene glycol-n-propylether, ethylene glycol phenyl ether, ethylene glycol mono-2-ethylhexyl ether, ethylene glycol monoethyl ether, glycerin, diethylene glycol, diethylene glycol-n-hexy-lether, diethylene glycolmethylether, diethylene glycol monoethyl ether, dietheylene glycol monobutyl ether, diethylene glycol monomethyl ether, diglycerin, dipropylene glycol, dipropylene glycol, dipropylene glycol-n-propyl-ether, dipropylene glycol monomethylether, dimethylsulfoxide, sulfolane, thiodiglycol, tetraethylene glycol, triethylene glycol, triethylene glycol ethylether, triethylene glycol dimethylether, triethylene glycol monobutylether, triethylene glycol methylether, tripropylene glycol, tripropylene glycol-n-propylether, tripropylene glycol methylether, trimethylol ethane, trimethylol propane, propylpropylene diglycol, propylene glycol, propylene glycol-n-butylether, propylene glycol-t-butylether, propyleneglycol phenylether, propylene glycol monoethylether, hexylene glycol, polyethylene glycol, and polypropylene glycol. These can be used alone or in combination.

The content of the organic solvent is preferably from 1 percent by mass to 40 percent by mass to the total amount of a hydrogel liquid precursor and more preferably from 5 percent by mass to 20 percent by weight.

Other Components

The other optional components have no particular limit. For example, known photopolymerizable initiators, surfactants, colorants, stabilizers, water-soluble resins, alcohols having low boiling points, surface treatment agents, viscosity adjusting agents, adherence imparting agents, anti-oxidants, anti-aging agents, cross-linking promoters, ultraviolet absorbents, plasticizers, and preservatives.

Property of Hydrogel Liquid Precursor

The surface tension of the hydrogel liquid precursor at 25 degrees C. is not particularly limited and is preferably from 20 mN/m to 45 mN/m and more preferably from 25 mN to 34 mN/m.

When the surface tension is 20 mN/m or more, dischargeability of the hydrogel liquid precursor is good when modeling a 3D object. When the surface tension is 45 mN/m or less, the property of the hydrogel liquid precursor is good when a discharging nozzle, etc. is filled with the hydrogel liquid precursor.

The surface tension can be measured by a surface tensiometer (automatic contact angle DM-701, manufactured by Kyowa Interface Science Co., LTD.), etc.

The viscosity of the hydrogel liquid precursor at 25 degrees C. at normal pressure is preferably 20 mPa·s or less and more preferably from 6 mPa·s to 12 mPa·s. The normal pressure means an air pressure of from 900 hPa to 1,100 hPa.

When the viscosity is in the range of from 3 mPa·s to 20 mPa·s, dischargeability of the hydrogel liquid precursor is good when modeling a 3D object.

The viscosity can be measured by, for example, a rotation viscometer (VISCOMATE VM-150 III, manufactured by TOKI SANGYO CO., LTD.) in a 25 degrees C. and normal pressure environment.

When the viscosity of the hydrogel liquid precursor at 25 degrees C. is defined as the initial viscosity and the two-week viscosity is defined as the viscosity at 25 degrees C. of the hydrogel liquid precursor left at 50 degrees C. for two weeks, the ratio of the two week viscosity to the initial viscosity is from 0.90 to 1.10.

When the ratio of the two week viscosity to the initial viscosity is from 0.90 to 1.10, storage stability of the hydrogel liquid precursor is appropriate and viscosity of the hydrogel liquid precursor containing a large amount of the inorganic mineral is maintained low, so that the hydrogel liquid precursor is suitably used for a liquid set for 3D modeling and a manufacturing method of a 3D modeling object.

The ratio of the two week viscosity to the initial viscosity can be calculated as follows.

First, the hydrogel liquid precursor is prepared, placed in a polypropylene bin (50 ml), left in a constant temperature tank at 50 degrees C. for 24 hours, and thereafter taken out from the tank to be cooled down to room temperature (25 degrees C.). Thereafter, the initial viscosity is measured at normal pressure.

In the case of the two week viscosity, the hydrogel liquid precursor is placed in a polypropylene bin (50 ml), left in a constant temperature tank at 50 degrees C. for two weeks, and thereafter taken out from the tank to be cooled down to room temperature (25 degrees C.) followed by measuring at normal pressure.

From the two-week viscosity and the initial viscosity, the ratio of the two-week viscosity to the initial viscosity is calculated.

The hydrogel liquid precursor of the present disclosure can be suitably used for methods of manufacturing various hydrogel modeling objects and in particular the hydrogel modeling object of the present disclosure, the liquid set for 3D modeling of the present disclosure, and the method of manufacturing 3D object of the present disclosure.

Liquid Set for 3D Modeling

The liquid set for 3D modeling of the present disclosure contains a hydrogel liquid precursor (first hydrogel liquid precursor) described above, a second hydrogel liquid precursor, preferably a liquid for a hard modeling object (support), and optionally other components.

The liquid set for 3D modeling makes it possible to provide a hydrogel modeling object having portions with different elasticity (80 percent compressive stress-strain or modulus of compressive elasticity), which is suitable as internal organ model.

First Hydrogel Liquid Precursor

The hydrogel liquid precursor of the present disclosure can be used as the first hydrogel liquid precursor.

Second Hydrogel Liquid Precursor

The second hydrogel liquid precursor contains a (second) inorganic mineral and a (second) monomer and has a different composition from the first hydrogel liquid precursor. The inorganic minerals and the monomers contained in the hydrogel liquid precursor of the present disclosure can be used as the second inorganic mineral and the second monomer "The second hydrogel liquid precursor has a different composition" means that either or both of the kind and the content of the composition constituting the second hydrogel liquid precursor is different from those of the first hydrogel liquid precursor.

It is preferable that the first hydrogel liquid precursor and the second hydrogel liquid precursor should form hydrogel modeling objects having different modulus of elasticity (80 percent compressive stress-strain or modulus of compressive elasticity) when these liquids are cured. For this reason, it is possible to efficiently manufacture a 3D modeling object having modeled portions having different modulus of elasticity.

Liquid for Hard Modeling Object (Support)

The liquid for a hard 3D object (support) is used in a method of manufacturing a 3D object and becomes a hard modeling object (support) to support a hydrogel modeling object during manufacturing in the manufacturing process of the 3D object. The liquid for a hard modeling object contains a curable material, preferably a photopolymerizable initiator, and other optional components but no water or inorganic mineral.

Curable Materials

The curable material is preferably a compound cured in polymerization reaction caused by irradiation of active energy ray (ultraviolet ray, electron beam, etc.), heating, etc. For example, active energy ray polymerizable compounds and thermally-curable compounds are suitable. Of these, materials being liquid at 25 degrees C. are preferable.

The active energy ray polymerizable compound is a monomer having a radically-polymerizable unsaturated bond in the molecule structure and a relatively low viscosity. It is possible to select from the multi-functional monomers or mono-functional monomers used in the first hydrogel liquid precursor and the second hydrogel liquid precursor to a particular application. These can be used alone or in combination.

The content of the curable material has no particular limit and can be selected to a particular application.

Other Components

The other optional components have no particular limit. For example, colorants, water-soluble resins, alcohols having low boiling points, surfactants, viscosity adjusting agents, adherence imparting agents, anti-oxidants, anti-aging agents, cross-linking promoters, ultraviolet absorbents, plasticizers, and dispersants.

The liquid set for 3D modeling of the present disclosure can be suitably used for manufacturing various 3D modeling objects and in particular, complex and fine 3D modeling objects having modeled portions having different modulus of elasticity (80 percent compressive stress-strain and modulus of compressive elasticity) such as internal organ model.

Also, the liquid is particularly suitable for the method of manufacturing a 3D object of the present disclosure and the hydrogel modeling object of the present disclosure.

Method of Manufacturing 3D Object

The method of manufacturing a 3D object of the present disclosure is to manufacture a hydrogel modeling object using the hydrogel liquid precursor or the liquid set for 3D modeling.

By the method of manufacturing a 3D object, complex and fine 3D objects represented by internal organ models are simply and efficiently manufactured.

The method of manufacturing a 3D object relating to a first embodiment includes a step of manufacturing a hydrogel modeling object using the hydrogel liquid precursor or the first hydrogel liquid precursor in the liquid set for 3D modeling and other optional steps such as curing the hydrogel liquid precursor or the first hydrogel liquid precursor.

The step of curing the liquid for 3D modeling is to cure the (first) hydrogel liquid precursor.

As the device to cure the (first) hydrogel liquid precursor, ultraviolet (UV) irradiating lamps, electron beam irradiators, etc. are used. The device to cure the (first) hydrogel liquid precursor preferably includes an ozone removing mechanism.

The ultraviolet irradiating lamp includes, for example, a high pressure mercury lamp and an ultra high pressure mercury lamp, and a metal halide lamp.

The ultra-high pressure mercury lamp is a point light source but if the DeepUV type in which the lamp is combined with an optical system to improve the light use efficiency is used, the lamp is capable of irradiating a short-wavelength modeling portion.

The metal halide lamp is suitable for a colored material because the colored material absorbs light so that irradiation of light outside the absorption band is possible for curing. Halogenized compounds of metal such as Pb, Sn, and Fe are used and can be selected to the absorption spectrum of a photopolymerization initiator.

The lamp for use in curing has no particular limit. Lamps available on market such as H lamp, D lamp, or V lamp, (manufactured by Fusion System) can be used to a particular application.

The method of manufacturing a 3D object relating to a second embodiment includes a step of placing the (first) hydrogel liquid precursor on a base plate (substrate) or a previously formed layer of the (first) hydrogel liquid precursor, curing the (first) hydrogel liquid precursor on the base plate or the layer, and other optional steps.

The method of placing the (first) hydrogel liquid precursor on the base is not particularly limited. Preferably, droplets formed of the (first) hydrogel liquid precursor are applied to target positions with appropriate precision by the method. For example, a dispenser method, a spray method, or an inkjet method can be suitably selected to a particularly application. Known devices are used to execute the method. Of these, the inkjet method is particularly preferable in the present disclosure. The inkjet method has a good quantitative property in comparison with the spray method and a wider application area in comparison with the dispenser method. Accordingly, the inkjet method is preferable to accurately and efficiently form a complex hydrogel modeling object.

With regard to the device to cure the (first) hydrogel liquid precursor, the detailed description is omitted because the curing device is the same as the device to cure the (first) hydrogel liquid precursor specified in the method of manufacturing a 3D object relating to the first embodiment.

The (first) hydrogel modeling object after curing has a three-dimensional network structure formed by complexing a polymer polymerized from the mono-functional monomer or the multi-functional monomer and the inorganic mineral. The three-dimensional network structure encloses water and components dissolved in the water.

In the method of manufacturing a 3D object relating to the second embodiment, each step described above may be repeated multiple times. When modeling an object by the repetition, the number of the repetition is not simply determined because the number depends on the side, form, structure, etc. of the 3D object to be manufactured. However, if the thickness per layer is in the range of from 10 μm to 50 μm, modeling can be precisely conducted free of peeling. Therefore, the layer is repetitively formed until the thickness of the laminated layers reaches the height of the 3D object to be manufactured.

The method of manufacturing a 3D object relating to a third embodiment preferably includes a step of forming a first modeled portion and a step of forming a second modeled portion, and other optional steps.

Step of Forming First Modeled Portion

The step of forming the first modeled portion includes placing the first hydrogel liquid precursor on a base plate (substrate) and curing the first hydrogel liquid precursor placed on the base plate.

With regard to the step of placing the first hydrogel liquid precursor on the base plate, the detailed description is omitted because the placing step is the same as the placing step of the first hydrogel liquid precursor on the base plate in the method of manufacturing the 3D object relating to the second embodiment.

The first hydrogel liquid precursor in the liquid set for 3D modeling of the present disclosure can be used as the first hydrogel liquid precursor.

The device to cure the first hydrogel liquid precursor on the base plate has no particular limit. For example, the curing step is the same as the curing step of the first hydrogel liquid precursor in the method of manufacturing the 3D object relating to the second embodiment.

Step of Forming Second Modeled Portion

The step of forming the second modeled portion includes placing the second hydrogel liquid precursor having the different composition from the first hydrogel liquid precursor on an area other than the area where the first hydrogel liquid precursor is placed and curing the second hydrogel liquid precursor placed on the base plate.

The second hydrogel liquid precursor may be the same as the first hydrogel liquid precursor except for the composition. "The second hydrogel liquid precursor has a different composition from the first hydrogel liquid precursor" means that either or both of the kind and the content of the composition constituting the second hydrogel liquid precursor is different from the first hydrogel liquid precursor. This makes it possible to manufacture a hydrogel modeling object having portions having different modulus of elasticity (80 percent compressive stress-strain) when both the first hydrogel liquid precursor and the second hydrogel liquid precursor are cured. Although depending on the purpose of application, one of the cured portions from the first hydrogel liquid precursor and the second hydrogel liquid precursor has an 80 percent compressive stress-strain of 0.4 mPa or more. The 80 percent compressive stress-strain can be measured by, for example, a universal tester (AG-I, manufactured by Shimadzu Corporation).

"Placing the second hydrogel liquid precursor on an area other than the area where the first hydrogel liquid precursor is placed" means that the position where the second hydrogel liquid precursor is placed does not overlap on the position where the first hydrogel liquid precursor is placed but the positions can be adjacent to each other.

The second hydrogel liquid precursor in the liquid set for 3D modeling of the present disclosure can be used as the second hydrogel liquid precursor.

The method of placing the second hydrogel liquid precursor is not particularly limited. Preferably, droplets formed of the second hydrogel liquid precursor are applied to target positions with appropriate precision by the method. For example, a dispenser method, a spray method, or an inkjet method can be suitably selected to a particularly application.

Curing of the first hydrogel liquid precursor on the base plate and curing of the second hydrogel liquid precursor on the base plate can be conducted at the same time or separately. In terms of production efficiency, it is preferable to conduct both curing at the same time.

Other Optional Steps

The other optional steps are not particularly limited and include for example, placing and curing a liquid for a hard modeling object (support) that becomes a hard modeling object to support a 3D object on a position on the base plate other than the positions of the first hard modeling object and the second hard modeling object, data processing of acquiring and processing three-dimensional data, removing the 3D object from the hard modeling object, cleaning the 3D object, and polishing the 3D object.

The liquid for a hard modeling object (support) in the liquid set for 3D modeling of the present disclosure can be used as the liquid for a hard modeling object (substrate).

"Placing the liquid for a hard modeling object on a position on the base other than the positions of the first hydrogel liquid precursor and the second hydrogel liquid precursor" means that the position where the liquid for a hard modeling object is placed does not overlap on the positions where the first hydrogel liquid precursor and the second hydrogel liquid precursor are placed but the position of the liquid for a hard modeling object may be adjacent to the positions of the first hydrogel liquid precursor and the second hydrogel liquid precursor.

The method of placing the liquid for a hard modeling object on the base is not particularly limited. Preferably, droplets formed of the liquid for a hard modeling object are applied to target positions with appropriate precision by the method. For example, a dispenser method, a spray method, or an inkjet method can be suitably selected to a particularly application.

In the method of manufacturing a 3D object relating to the third embodiment, each step described above may be repeated multiple times. When repeating each step, the number of the repetition to form a 3D object by laminating layers on the base plate is not simply determined because the number depends on the side, form, structure, etc. of the 3D object to be manufactured. However, if the thickness per layer is in the range of from 10 μm to 50 μm, modeling can be precisely conducted free of peeling. Therefore, the layer is repetitively formed until the thickness of the laminated layers reaches the height of the 3D object to be manufactured.

As for the data processing step, for example, the method disclosed in Japanese Patent No. 5239037 can be used. In the present disclosure, from acquiring data to discharging each liquid using the liquid set for 3D modeling is conducted as follows.

First, three-dimensional surface data or solid data designed by three-dimensional computer-aided designing system (CAD) or taken in by a three-dimensional scanner or digitizer are converted into standard triangulated language (STL) format to obtain various data. Thereafter, the obtained data are input into a device for 3D modeling. Based on the various kinds of input data, the direction of 3D modeling is determined for a 3D object to be modeled. The direction is not particularly limited. Normally, it is preferable to select a direction in which Z direction (height direction) is the lowest.

After determining the direction of the modeling, the projected areas in X-Y plane, X-Z plane, and Y-Z plane of the three-dimensional form are obtained. To reinforce the thus-obtained block form, each plane except for the upper plane of the X-Y plane is transferred to the outside direction in a suitable amount. The transfer amount is not particularly limited and is, for example, about 1 mm to about 10 mm although depending on the form, the size, and material. The block form enclosing the form to be modeled is identified except for the upper plane.

This block form is sliced in the Z direction with a thickness of a single layer. The thickness of a single layer varies depending on materials and cannot be simply determined but is preferably from 10 μm to 50 μm. When only one 3D object is manufactured, this block form is placed in the center of the Z stage (i.e., table on which the modeled object lowered a single layer by a single layer for each layer forming is placed).

In addition, when a plural of 3D objects are manufactured at the same time, the block forms are arranged on the Z stage. Also, the block forms can be piled up. It is possible to automatically create the block forms, the sliced data (contour line data), and the placement on the Z stage if materials to be used are determined.

Next, by the in-or-out decision (whether to jet each liquid of the liquid set for 3D modeling described above on the contour) with reference to the outermost contour line of the sliced data, the positions where each liquid is jetted in an inkjet method are controlled.

The sequence of jetting the liquids in the liquid set for 3D modeling is, for example, when liquids from the first to the liquid for hard modeling object are used, it is preferable to jet the liquid for hard modeling object first and thereafter at least one of the first hydrogel liquid precursor and the second hydrogel liquid precursor. If the liquids are jetted in this sequence, storage portions such as gutters and dams are formed by the liquid for hard modeling object. Thereafter, at least one of the first hydrogel liquid precursor and the second hydrogel liquid precursor are jetted into the storage portion, so that even if materials which are liquid at room temperature are used as the first hydrogel liquid precursor and the second hydrogel liquid precursor, the liquid does not drip off. Therefore, a wide variety of photocurable resins, thermocuring resins, etc. can be used.

In addition, to shorten the modeling time, it is preferable to jet at least one of the first hydrogel liquid precursor, the second hydrogel liquid precursor, and the liquid for hard modeling object in each of outward and return routes of integrated inkjet heads for lamination. Furthermore, by using a mechanism having an active energy ray irradiator (for example, ultraviolet irradiator) adjacent to an inkjet head to jet each liquid of the liquid set for 3D modeling, the time to be taken for smoothing treatment is omitted, thereby speeding up the modeling.

As described above, in the method of manufacturing a 3D object of the present disclosure, the liquid is discharged through fine holes by an inkjet method or disperser method so that the liquid is applied to form an image for a single layer. Therefore, at least one of the first hydrogel liquid precursor and the second hydrogel liquid precursor is clearly separated from and not mixed with the liquid for hard modeling object at the border before curing (non-compatible state).

In typical modeling methods, at least one of the first hydrogel liquid precursor and the second hydrogel liquid precursor is compatibilized with the liquid for hard modeling object at contact portions so that the border is not clear when photopolymerized. As a result, fine concavo-convex portions remain on the surface of the thus-obtained 3D object. To the contrary, according to the method of manufacturing a 3D object of the present disclosure, the border after photopolymerization is clear because at least one of the first hydrogel liquid precursor and the second hydrogel liquid precursor is not compatible with the liquid for hard modeling object. Furthermore, due to the difference of hardness between the thus-obtained 3D object and the hard modeling object, the 3D object is easily separated (peeled) from the hard modeling object. Therefore, the surface smoothness of the 3D object is improved, thereby completely or significantly omitting the polishing step after modeling.

Figure 4A:
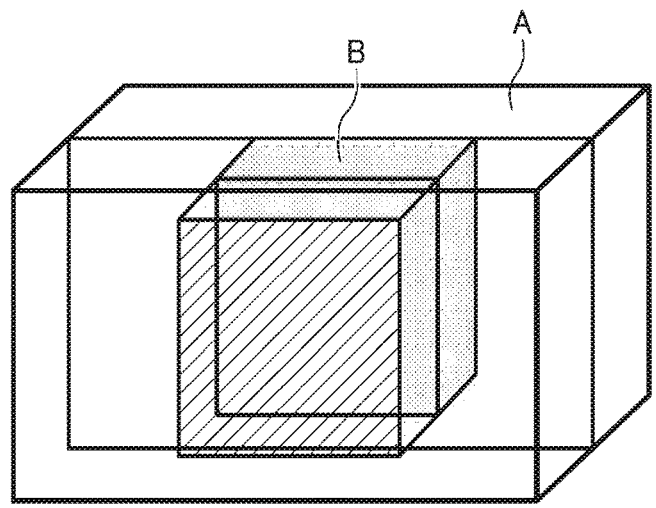
FIG. 4A is a schematic diagram illustrating an example of the 3D object manufactured by the method of manufacturing a 3D object according to an embodiment of the present invention.
Figure 4B:
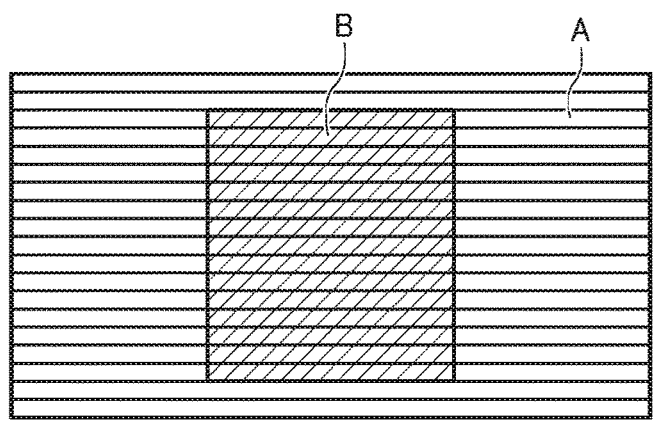
FIG. 4B is a schematic cross sectional view of the 3D object illustrated in FIG. 4A.

It is preferable that, in the hydrogel modeling object manufactured by the method of manufacturing a 3D object of the present disclosure, the first modeled portion (modeled portion A) should completely contain the second modeled portion (modeled portion B) as described in FIGS. 4A and 4B. "The modeled portion A should completely contain the second modeled portion B" means the first modeled portion is wholly adjacent and encloses the second modeled portion.

The hydrogel modeling object obtained by the method of manufacturing a 3D object is highly elastic and has a complex internal structure represented by internal organ modes. Therefore, this object is suitable as the internal organ model. The internal organ model truly reproduces the internal structure of vessels and areas of pathology having different hardness and modulus of elasticity and the bite and touch of the model are extremely close to those of an internal organ. Furthermore, since the model can be cut open by a surgical scalpel, the model is particularly suitable for procedure practice.

Device for 3D Modeling

Figure 2:
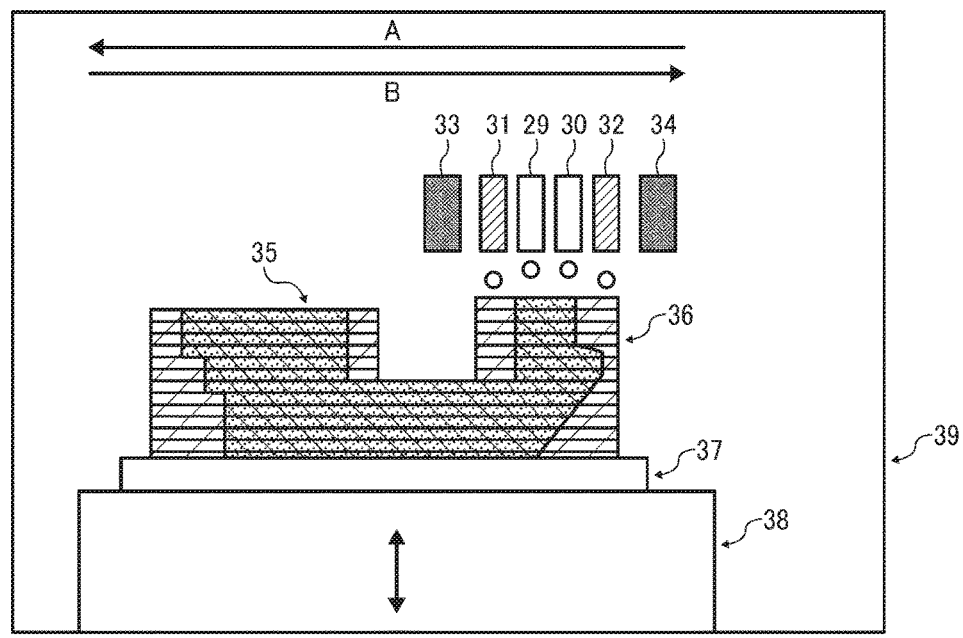
FIG. 2 is a schematic diagram illustrating an example of the device for manufacturing a 3D object for use in the method of manufacturing a 3D object according to an embodiment of the present invention.

FIG. 2 is a schematic diagram illustrating an example of the device for 3D modeling for use in the present disclosure.

A device for 3D modeling illustrated in FIG. 2 jets at least one of the first hydrogel liquid precursor and the second hydrogel liquid precursor from jetting head units 29 and 30 for modeling and the liquid for hard modeling object from jetting head units 31 and 32 for support using head units in which inkjet heads are arranged. The device also laminates each liquid of the liquid set for 3D modeling while curing the liquid set with adjacent ultraviolet ray irradiators 33 and 34.

The liquid for a hard modeling object is jetted from the jetting head units 31 and 32 for support and solidified to form a first substrate layer having a storage portion. Thereafter, at least one of the first hydrogel liquid precursor and the second hydrogel liquid precursor is jetted from the head units 29 and 30 for 3D modeling to the storage portion of the first substrate layer and irradiated with an active energy ray to form a first modeling object layer. The liquid for a hard modeling object is jetted onto the first substrate layer and solidified to form the second substrate layer having a storage portion on the first substrate layer. Thereafter, at least one of the first hydrogel liquid precursor and the second hydrogel liquid precursor is jetted onto the storage portion of the second substrate layer and irradiated with an active energy ray to form a second modeling object layer on the first modeling object layer to form a 3D object 35.

When the multi-head unit moves in the direction indicated by the arrow A, a support 36 and the 3D object 35 are formed on a 3D object base plate (substrate) 37 using the jetting head unit 31 for substrate, the jetting head units 29 and 30 for 3D modeling, and the ultraviolet ray irradiator 34. The jetting head unit 32 for support and the ultraviolet ray irradiator 33 may be auxiliarily used.

When the multi-head unit moves in the direction indicated by the arrow B, the support 36 and the 3D object 35 are formed on the 3D object base plate 37 using the jetting head unit 32 for support, the jetting head units 29 and 30 for 3D modeling, and the ultraviolet rate irradiator 33. The jetting head unit 31 for support and the ultraviolet ray irradiator 34 may be auxiliarily used.

Furthermore, to keep the gap between the jetting head units 29 and 30 for 3D modeling, the jetting head units 31 and 32 for support, and the ultraviolet ray irradiators 33 and 34 and the 3D object 35 and the substrate 36, a stage 38 is lowered to the number of lamination.

Figure 3:
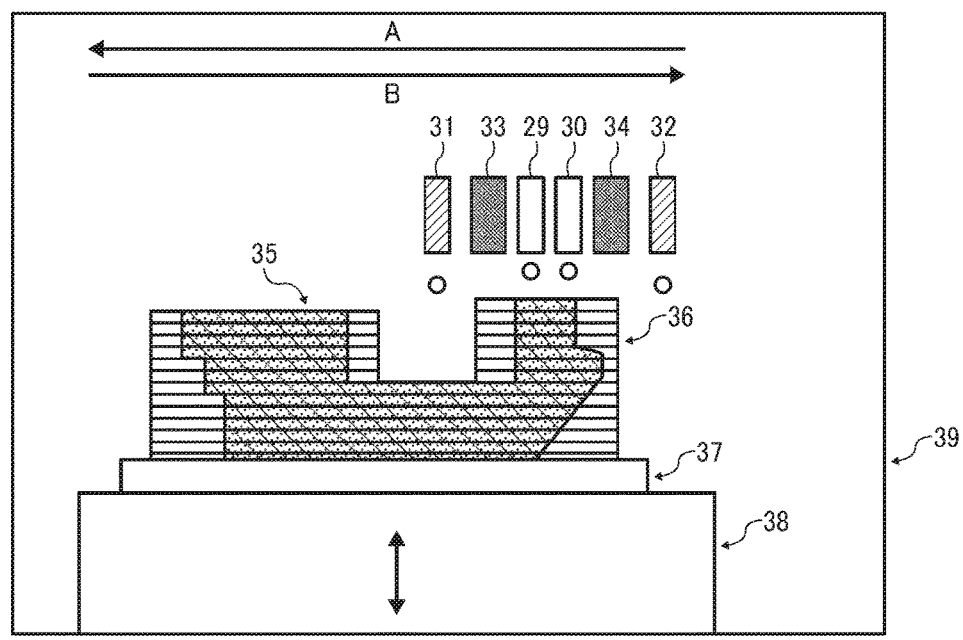
FIG. 3 is a schematic diagram illustrating another example of the device for manufacturing a 3D object for use in the method of manufacturing a 3D object according to an embodiment of the present invention.

FIG. 3 is a schematic diagram illustrating another example of the 3D object manufacturing mechanism to improve smoothness of each layer in comparison with that illustrated in FIG. 2. Basically, the process is the same as in FIG. 2 but unlike the configuration illustrated in FIG. 2, the ultraviolet ray irradiators 33 and 34 are disposed between the jetting head units 29 and 30 for 3D modeling and the jetting head units 31 and 32 for support.

In addition, in the device 39 for 3D modeling, the ultraviolet ray irradiators 33 and 34 are used in both directions of the arrows A and B. Due to heat generated upon application of ultraviolet ray, the surface of the liquid for the laminated hard modeling object is smoothed, thereby improving the dimension stability of the hydrogen modeling object.

In addition, the device 39 for 3D modeling may furthermore include devices for collecting ink, recycling, etc. Also, the device 39 optionally includes a blade to remove each of the liquid precursors of the liquid set for 3D modeling attached to the nozzle surface or detector to detect un-discharging nozzles. Furthermore, it is preferable to control the environment temperature in the device 39 during modeling.

Hydrogel Modeling Object

The hydrogel modeling object includes an inorganic mineral, a phosphonic acid compound, a polymer, preferably a solvent, and other optional components.

Inorganic Mineral

The inorganic mineral contained in the hydrogel liquid precursor can be used as the inorganic mineral.

The content of the inorganic mineral is preferably 15 percent by mass or more, preferably from 15 percent by mass to 40 percent by mass, and more preferably from 15 percent by mass to 25 percent by weight to the total amount of hydrogel modeling object. When the content is 15 percent by mass or more, it is possible to increase the modulus of elasticity of the hydrogel modeling object.

The content of the inorganic mineral can be obtained by heating and drying the hydrogel modeling object by a thermal analyzer (TG/DTA, manufactured by Rigaku Corporation) followed by analysis on the residual component.

Polymer

As the polymer, polymers having, for example, an amide group, an amino group, a hydroxyl group, a tetramethyl ammonium group, a silanol group, an epoxy group, etc. are suitable and the polymer is preferably water soluble.

Homopolymers (monopolymers), heteropolymers (copolymers), modified resins, or forms of salts are also allowed. Also, known functional groups can be introduced into these. Of these, homoplymers are preferable.

Water-solubility of the polymer in the present disclosure means, for example, when 1 g of the polymer is mixed with and stirred in 100 g of water at 30 degrees C., 90 percent by mass or more of the polymer is dissolved in water.

The polymer is obtained by polymerizing the monomer. The hydrogel modeling object is preferably formed of a hydrogel containing a solvent in a three-dimensional network structure formed by cross-linking the inorganic mineral dispersed in the solvent with the polymer obtained by polymerizing the monomer.

Phosphonic Acid Compound

The phosphonic acid contained in the hydrogel liquid precursor can be used as the phosphonic acid compound.

Solvent

The solvent that can be used for the hydrogel modeling object can be used as the solvent. Of these, water is preferable.

Properties of Hydrogel Modeling Object

The hydrogel modeling object of the present disclosure preferably has an 80 percent compressive stress-strain of 1.0 MPa or more, more preferably 2.0 MPa or more, and particularly preferably 3.0 MPa or more. The upper limit is not particularly limited and suitably determined to a particular application. For example, 10 MPa or less is preferable for an internal organ model. When the 80 percent compressive stress-strain is 1.0 Mpa or more, the hydrogel modeling object is highly elastic and reproduces hardness close to textures of a live body. That is, a more real internal organic model can be provided.

The modulus of compressive elasticity of the hydrogel modeling object is preferably from 0.1 MPa to 1.0 MPa and more preferably from 0.3 MPa to 0.8 MPa. When the modulus of compressive elasticity is within the preferable range specified above, the hydrogel modeling object is highly elastic and reproduces hardness close to textures of a live body. That is, a more real internal organic model can be provided.

The 80 percent compressive stress-strain and the modulus of compressive elasticity can be measured by, for example, a universal tester (AG-I, manufactured by Shimadzu Corporation). The 80 percent compressive stress-strain and the modulus of compressive elasticity are measured by providing a load cell of 1 kN and a compression jig for 1 kN to the universal tester. The sample for use in measuring by the universal tester has a form of a cube having a dimension of 10 mm×10 mm×10 mm.

The hydrogel modeling object of the present disclosure has a first modeled portion including the first hydrogel modeling object as the first modeling object and the second modeled portion including the second hydrogel modeling object having a different modulus of elasticity (80 percent compressive stress-strain or modulus of compressive elasticity) from that of the first hydrogel modeling object.

As a result, the thus-obtained hydrogel modeling object has portions having different modulus of elasticity (80 percent compressive stress-strain or modulus of compressive elasticity) therein. In the hydrogel modeling object, the first modeled portion may completely contain the second modeled portion or vice versa. Alternatively, the first modeled portion or the second modeled portion may be exposed. A 3D object in which one modeled portion wholly contains the other is particularly efficiently manufactured by a method laminating hydrogel thin layers formed by discharging and curing each liquid precursor by an inkjet method.

Having generally described preferred embodiments of this invention, further understanding can be obtained by reference to certain specific examples which are provided herein for the purpose of illustration only and are not intended to be limiting. In the descriptions in the following examples, the numbers represent weight ratios in parts, unless otherwise specified.

EXAMPLES

Next, the present disclosure is described in detail with reference to Examples but is not limited thereto.

Example 1

Manufacturing of Hydrogel Liquid Precursor 1

Based on the compositions shown in Table 1, [Hydrogel liquid precursor 1] was prepared as follows.

Preparation of Water

Pure water was prepared by evacuating deionized water for ten minutes.

Preparation of Liquid of Initiator

An aqueous solution was prepared as [Liquid 1 of initiator] by dissolving a photopolymerization initiator (IRGACURE 184, manufactured by BASF) in ethanol in a ratio of 4 parts of the photopolymerization initiator to 96 parts of ethanol.

An aqueous solution was prepared as [Liquid 2 of initiator] by dissolving sodium peroxodisulfate (manufactured by Wako Pure Chemical Industries, Ltd.) in pure water in a ratio of 2 parts of the photopolymerization initiator to 98 parts of ethanol.

Tetraethyl methylene diamine (manufactured by Wako Pure Chemical Industries, Ltd.) was used as [Liquid 3 of initiator].

Preparation of Hydrogel Liquid Precursor 1

While stirring 165 parts of pure water, 20 parts of synthesized hectorite (laponite XLG, manufactured by Rock-Wood) having a composition of $[Mg_{5.34}Li_{0.66}Si_8O_{20}(OH)_4]$ $Na^-_{0.66}$ as laminate mineral was slowly dripped and added to the pure water followed by stirring to prepare a liquid dispersion.

Next, 0.8 parts of etidronic acid aqueous solution (CHELEST PH-210, content of effective component: 60 percent by mass, manufactured by CHELEST CORPORATION) was added to the thus-obtained liquid dispersion. Subsequent to 30-minute dispersion, 20 parts of the synthesized hectorite was furthermore gradually added thereto followed by 30-minute stirring. 40 parts of the synthesized hectorite was added in total. Thereafter, the liquid dispersion was stored in a constant temperature tank at 50 degrees C. for ten hours to stabilize the dispersion.

Next, 20 parts of acryloyl morpholine (ACMO, manufactured by KJ Chemicals Corporation) from which the polymerization inhibitor was removed by passing through active alumina column as the monomer and 30 parts of glycerin were added to the thus-obtained liquid dispersion. Furthermore, 10 parts of EMALGEN SLS-106 (manufactured by Kao Corporation) serving as surfactant was admixed with the resultant.

Next, 2.2 parts of the [Liquid 1 of initiator] and 0.15 parts of the [Liquid 3 of initiator] were added to the mixture while being cooled down. Subsequent to stirring and mixing, the resultant was subject to evacuation for 20 minutes. Thereafter, impurities were removed by filtration to prepare [Hydrogel liquid precursor 1].

Storage Stability

The thus-obtained [Hydrogel liquid precursor 1] was placed in polypropylene bin (50 ml) and left in a constant temperature tank at 50 degrees for 24 hours. The [Hydrogel liquid precursor 1] was taken out of the constant temperature tank and left until the temperature of the [Hydrogel liquid precursor 1] was down to room temperature (25 degrees C.). The initial viscosity of [Hydrogel liquid precursor 1] was measured under 1 atm.

The [Hydrogel liquid precursor 1] was placed in a polypropylene bin (50 ml), left in a constant temperature tank at 50 degrees C. for two weeks, and thereafter taken out from the tank. The [Hydrogel liquid precursor 1] taken out of the constant temperature tank was left and cooled down to room temperature (25 degrees C.) followed by measuring the two-week viscosity at 1 atm. The ratio of the two-week viscosity to the initial viscosity was calculated.

The measuring results of the initial viscosity and the two-week viscosity and the calculation results of the ratio of the two-week viscosity to the initial viscosity are shown in Table 1.

The initial viscosity and the two-week viscosity were measured by a rotation viscometer (VISCOMATE VM-150 III, manufactured by TOKI SANGYO CO., LTD.).

Compression Test

The thus-obtained [Hydrogel liquid precursor 1] was irradiated with a light amount of 350 mJ/cm$^2$ by an ultraviolet irradiator (SPOT CURE SP5-250DB, manufactured by USHIO INC.) to manufacture [Hydrogel modeling object 1]. 80 percent compressive stress-strain and modulus of compressive elasticity of the thus-obtained [Hydrogel modeling object 1] were measured as follows: The results are shown in Table 1.

[Hydrogel modeling object 1] having a form of 10 mm×10 mm×10 mm was placed in a universal tester (AG-1, manufactured by SHIMADZU CORPORATION). The stress to the compression applied to the load cell of the universal tester mentioned above was recorded by a computer to plot the stress to the amount of displacement.

When the hydrogel modeling object was fractured, the modulus of compressive elasticity at the time of the fracture was determined as the maximum value. The 80 percent compressive stress-strain was shown for the un-fractured hydrogel modeling object.

In addition, the modulus of compressive elasticity of the hydrogel modeling object was obtained from the measuring data from the same universal tester. The modulus of compressive elasticity was calculated as the gradient at 10 percent displacement taken as the difference between 10 percent compressive stress-strain and 20 percent compressive stress-strain.

Examples 2 to 7

[Hydrogel liquid precursor 2] to [Hydrogel liquid precursor 7] were prepared in the same manner as in Example 1 except that the composition and the blending amount of Example 1 were changed to the compositions and the blending amounts shown in Table 1.

With regard to the thus-obtained [Hydrogel liquid precursor 2] to [Hydrogel liquid precursor 7], the initial viscosity and the two-week viscosity were measured in the same manner as in Example 1 and the ratio of the two-week viscosity to the initial viscosity was calculated. The results are shown in Table 1.

Next, using the obtained [Hydrogel liquid precursor 2] to [Hydrogel liquid precursor 7], [Hydrogel modeling object 2] to [Hydrogel modeling object 7] were manufactured in the same manner as [Hydrogel modeling object 1].

The compression test was conducted for the [Hydrogel modeling object 2] to [Hydrogel modeling object 7] in the same manner as the [Hydrogel modeling object 1]. The results are shown in Table 1.

TABLE 1

| | | Example | | | | | | |
|---|---|---|---|---|---|---|---|---|
| Component (parts by mass) | | 1 | 2 | 3 | 4 | 5 | 6 | 7 |
| Hydrogel liquid precursor No. | | 1 | 2 | 3 | 4 | 5 | 6 | 7 |
| Hydrogel No. | | 1 | 2 | 3 | 4 | 5 | 6 | 7 |
| Inorganic mineral | XLG | 40 | 40 | 40 | 40 | 40 | 40 | 40 |
| Monomer | ACMO | 20 | 20 | 20 | 20 | 20 | 20 | 20 |
| Phosphonic acid compound | Etidronic acid | 0.8 | 0.8 | — | — | — | — | 0.8 |
| | Etidronic acid disodium | — | — | 0.32 | — | — | — | — |
| | Etidronic Acid tetra-sodium | — | — | — | 0.32 | — | — | — |
| | Alendronic acid | — | — | — | — | 0.32 | — | — |
| | Methylene diphosphonic acid | — | — | — | — | — | 0.32 | — |
| Surfactant | EMULGEN SLS-106 | 1 | 1 | 1 | 1 | 1 | 1 | 1 |
| Liquid 1 of initiator | IRGACURE 819 (4 percent in EtOH) | 2.2 | 2.2 | 2.2 | 2.2 | 2.2 | 2.2 | — |
| Liquid 2 of initiator | Sodium peroxodisulfate (2 percent aq) | — | — | — | — | — | — | 5 |
| Liquid 3 of initiator | Tetraethyl methylene diamine | 0.15 | 0.15 | 0.15 | 0.15 | 0.15 | 0.15 | 0.15 |

TABLE 1-continued

| Component (parts by mass) | | Example | | | | | | |
|---|---|---|---|---|---|---|---|---|
| | | 1 | 2 | 3 | 4 | 5 | 6 | 7 |
| Solvent | Glycerin | 30 | 30 | 30 | 30 | 30 | 30 | 30 |
| Water | Deionized water | 165 | 165 | 165 | 165 | 165 | 165 | 165 |
| Property of hydrogel liquid precursor | Initial viscosity (mPa·s) | 12.5 | 13.5 | 13.8 | 12.9 | 14.2 | 13.9 | 12.2 |
| | Two-week viscosity (mPa·s) | 12.3 | 13.8 | 13.8 | 13.4 | 14.6 | 13.9 | 12.6 |
| | Two-week viscosity/ Initial viscosity | 1.0 | 1.0 | 1.0 | 1.0 | 1.0 | 1.0 | 1.0 |
| Property of hydrogel | Modulus of compressive elasticity (MPa) | 0.75 | 0.69 | 0.72 | 0.68 | 0.73 | 0.23 | 0.85 |
| | 80 percent compressive stress-strain (MPa) | 4.3 | 3.8 | 3.2 | 3.7 | 3.8 | 4.1 | 6.5 |

The details of the phosphonic acid compounds shown in Table 1 were as follows:
Etidronic Acid Disodium (manufactured by CHELEST CORPORATION)
Etidronic Acid tetrasodium (manufactured by CHELEST CORPORATION)
Alendronic acid (Tokyo Chemical Industry Co. Ltd.)
Methylene diphosphonic acid (Tokyo Chemical Industry Co. Ltd.)

Comparative Examples 1 to 5

[Hydrogel liquid precursor 8] to [Hydrogel liquid precursor 12] were prepared in the same manner as in Example 1 except that the composition and the blending amount of Example 1 was changed to the compositions and the blending amounts shown in Table 2.

Next, using the obtained [Hydrogel liquid precursor 8] to [Hydrogel liquid precursor 12], [Hydrogel modeling object 8] to [Hydrogel modeling object 12] were manufactured in the same manner as [Hydrogel modeling object 1].

The compression test was conducted for the [Hydrogel modeling object 8] to [Hydrogel modeling object 12] in the same manner as the [Hydrogel modeling object 1]. The results are shown in Table 2.

TABLE 2

| Component (parts by mass) | | Comparative Example | | | | |
|---|---|---|---|---|---|---|
| | | 1 | 2 | 3 | 4 | 5 |
| Hydrogel liquid precursor No. | | 8 | 9 | 10 | 11 | 12 |
| Hydrogel No. | | 8 | 9 | 10 | 11 | 12 |
| Inorganic mineral | XLG | 40 | 40 | 40 | 40 | 40 |
| Monomer | ACMO | 20 | 20 | 20 | 20 | 20 |
| Phosphonic acid | Pyrophosphoric acid | 0.32 | — | — | 0.72 | — |
| | Phytic acid | — | 0.32 | — | — | — |
| | NTMP | — | — | 0.32 | — | — |
| Surfactant | EMULGEN SLS-106 | 1 | 1 | 1 | 1 | 1 |
| Water | IRGACURE 819 | 2.2 | 2.2 | 2.2 | 2.2 | 2.2 |
| Liquid 1 of initiator | Deionized water | 165 | 165 | 165 | 165 | 165 |
| Property of hydrogel liquid precursor | Initial viscosity (mPa·s) | 12.3 | 368 | 152 | Gelated | Gelated |
| | Two-week viscosity (mPa·s) | Gelated | Gelated | Gelated | Gelated | Gelated |
| | Two-week viscosity/ Initial viscosity | —* | —* | —* | —* | —* |

TABLE 2-continued

| Component (parts by mass) | | Comparative Example | | | | |
|---|---|---|---|---|---|---|
| | | 1 | 2 | 3 | 4 | 5 |
| Property of hydrogel | Modulus of compressive elasticity (MPa) | 0.09 | —** | —** | —** | —** |
| | 80 percent compressive stress-strain (MPa) | 1.2 | —** | —** | —** | —** |

—* represents "unable to calculate due to gelation"
—** represents "unable to measure"

The details of the phosphonic acid compounds shown in Table 2 were as follows:

Pyrophosphoric acid (manufactured by Sigma-Aldrich Japan K.K.)

Phytic acid (manufactured by Tokyo Chemical Industry Co. Ltd.)

Nitrilotris (Methylene Phosphonic Acid (NTMP, manufactured CHELEST CORPORATION)

In Comparative Examples 2 and 3 shown in Table 2, hydrogels were not modeled from [Hydrogel liquid precursor 9] or [Hydrogel liquid precursor 10] because these liquids had excessively high initial viscosity. In addition, [Hydrogel liquid precursor 11] and [Hydrogel liquid precursor 12] of Comparative Examples 4 and 5 were gelated during preparation of the hydrogel liquid precursor so that it was not possible to prepare hydrogel liquid precursors or measure the viscosity thereof.

Example 8

Using the [Hydrogel liquid precursor 1] and [Hydrogel liquid precursor 2] and the device for 3D modeling illustrated in FIG. 2, [3D object 1] illustrated in FIGS. 4A and 4B were manufactured. First, the 3D data of the 3D object as illustrated in FIGS. 4A and 4B were input into the device for 3D modeling.

The two tanks communicating with the inkjet heads of the device for 3D modeling (MH2420, manufactured by Ricoh Industry Company, Ltd.) were filled with the [Hydrogel liquid precursor 1] and [Hydrogel liquid precursor 2] and the two kinds of hydrogel precursor liquids were jetted from each inkjet heads to place the [Hydrogel liquid precursor 1] and [Hydrogel liquid precursor 2] on a base plate.

Next, the [Hydrogel liquid precursor 1] and [Hydrogel liquid precursor 2] placed on the base plate were irradiated with a light amount of 1,000 mJ/cm$_2$ by an ultraviolet irradiator (SubZero055, manufactured by Integration Technology Ltd.) to cure the [Hydrogel liquid precursor 1] and [Hydrogel liquid precursor 2] on the base plate. This series of steps were repeated to manufacture (model) the [3D object 1].

The thus-obtained [3D object] was cut to obtain cubes of 10 mm×10 mm×10 mm from the portions corresponding to the modeled portion B and the modeled portion A and the modulus of elasticity (80 percent compressive stress-strain and modulus of compressive elasticity) for each was measured. The modeled portion A had the modulus of elasticity (80 percent compressive stress-strain and modulus of compressive elasticity) around that of the [Hydrogel modeling object 1] and the modeled portion B had the modulus of elasticity (80 percent compressive stress-strain and modulus of compressive elasticity) around that of the [Hydrogel modeling object 2].

Example 9

Preparation of Liquid for Hard Modeling Object (Support)

A total content of 300 grams including 10 parts of urethane acrylate (product name: DIABEAM UK6038, manufactured by Mitsubishi Rayon Co., Ltd.) as curable material, 90 parts of neopentyl glycol hydroxy pivalic acid ester dimethacrylate (product name: KAYARAD MANDA, manufactured by Nippon Kayaku Co., Ltd.) as curable material, 3 parts of photopolymerization initiator (product name: IRGACURE 184, manufactured by BASF), and 2 parts of blue pigment (product name: Lionol Blue 7400G, manufactured by TOYO INK CO., LTD.) as colorant were dispersed at 2,000 rotation per minute (rpm) using a Homogenizer (HG30, manufactured by Hitachi Koki Co., Ltd.) until a uniform mixture was obtained. Thereafter, the mixture was filtered to remove impurities followed by evacuation in vacuum for ten minutes to obtain a liquid for hard modeling object (support).

Using the [Hydrogel liquid precursor] and the [Hydrogel liquid precursor 4], and the liquid for hard modeling object, data processing was conducted according to the description of Japanese Patent No. 5239037 by the device for 3D modeling illustrated in FIG. 2 to obtain the three-dimensional model data of a liver. Based on the model data, an internal organ model of the liver of a pig was manufactured (modeled).

The thus-obtained internal organ model of the liver was almost true to life of a real liver of the pig about form, touch, and elasticity.

Embodiments of the present disclosure are, for example, as follows.

1. A hydrogel liquid precursor includes an inorganic mineral and a monomer, wherein the inorganic mineral accounts for 15 percent by mass or more of the hydrogel liquid precursor, wherein the hydrogel liquid precursor has an initial viscosity of 20 mPa·s or less at 25 degrees C., wherein the hydrogel liquid precursor has a ratio of a two-week viscosity to the initial viscosity of from 0.90 to 1.10, the two-week 2. viscosity representing a viscosity of the hydrogel liquid precursor at 25 degrees C. after being left at 50 degrees C. for two weeks.

2. The hydrogel precursor liquid according to 1 mentioned above, further includes a phosphonic acid compound.

3. The hydrogel precursor liquid according to 2 mentioned above, wherein the phosphonic acid compound is represented by the following Chemical formula 1.

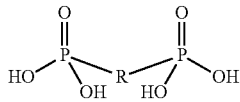

Chemical formula 1 where R represents a substituted or non-substituted divalent substitution group.

4. The hydrogel precursor liquid according to 3 mentioned above, wherein R in the Chemical formula 1 includes —($R_1$)C($R_2$)—, where $R_1$ and $R_2$ each, independently represent substituted or non-substituted alkyl groups.

5. The hydrogel precursor liquid according to 3 or 4 mentioned above, wherein R in the Chemical formula 1 includes —(OH)C($CH_3$)—.

6. The hydrogel precursor liquid according to any one of 1 to 5 mentioned above, wherein the monomer includes an active energy ray polymerizable monomer.

7. A method of manufacturing a three-dimensional object includes manufacturing a hydrogel modeling object using the liquid set of any one of 1 to 6 mentioned above.

8. A liquid set for three-dimensional modeling includes a first hydrogel liquid precursor including a first inorganic mineral and a first monomer, wherein the first inorganic mineral accounts for 15 percent by mass or more of the first hydrogel liquid precursor, wherein the first hydrogel liquid precursor has an initial viscosity of 20 mPa·s or less at 25 degrees C., wherein the first hydrogel liquid precursor has a ratio of a two-week viscosity to the initial viscosity of from 0.90 to 1.10, the two-week viscosity representing a viscosity of the first hydrogel liquid precursor at 25 degrees C. after being left at 50 degrees C. for two weeks, and a second hydrogel liquid precursor including a second inorganic mineral and a second monomer.

9. A method of manufacturing a three-dimensional object includes manufacturing a hydrogel modeling object using the liquid set for 3D modeling of 8 mentioned above.

10. The method according to 9 mentioned above, further includes placing the first hydrogel precursor liquid, placing the second hydrogel precursor liquid on a different position from where the first hydrogel precursor is placed, and repeating the placing the first hydrogel precursor and the placing the second hydrogel precursor multiple times.

11. The method according to 10 mentioned above, wherein one of the placing the first hydrogel precursor and the placing the second hydrogel precursor is conducted by an inkjet method or a dispenser method.

12. A hydrogel modeling object manufactured by the method of any one of 7, 9, 10, and 11 has an 80 percent compressive stress-strain of 1.0 MPa or more.

13. A hydrogel modeling object includes an inorganic mineral, a phosphonic acid compound, and a polymer, wherein the inorganic mineral accounts for 15 percent by mass or more of the hydrogel modeling object.

14. The hydrogel modeling object according to 13 mentioned above, has an 80 percent compressive stress-strain of 1.0 MPa or higher.

15. The hydrogel modeling object according to 13 or 14 mentioned above, wherein the inorganic mineral includes a laminate mineral.

16. The hydrogel precursor liquid according to any one of 13 to 15, wherein the phosphonic acid compound is represented by the following Chemical formula 1,

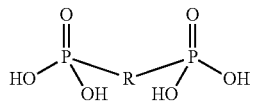

Chemical formula 1 where R represents a substituted or non-substituted divalent substitution group.

17. The hydrogel modeling object according to 16 mentioned above, wherein R in the Chemical formula 1 includes —($R_1$)C($R_2$)—, where $R_1$ and $R_2$ each, independently represent substituted or non-substituted alkyl groups.

18. The hydrogel modeling object according to 16 or 17 mentioned above, wherein R in the Chemical formula 1 includes —(OH)C($CH_3$)—.

19. A hydrogel modeling object includes a first modeled portion including the hydrogel modeling object of any one of 12 to 18 mentioned above and a second modeled portion including a second hydrogel modeling object having a different modulus of compressive elasticity from a compressive elasticity of the hydrogel modeling object of any one of 12 to 18 mentioned above, wherein the first modeled portion includes or is included in the second modeled portion.

20. The hydrogel modeling object according to any one of 12 to 19 mentioned above, wherein the inorganic mineral includes a laminate mineral.

According to the present disclosure, provide is an improved hydrogel liquid precursor having good storage property and suitable to manufacture a hydrogel modeling object having a complex inner structure including a modeling portion having a high modulus of elasticity shaped by a hydrogel modeling object having a high modulus of elasticity with a modeling portion having a low modulus of elasticity disposed at an arbitrary area.

Having now fully described embodiments of the present invention, it will be apparent to one of ordinary skill in the art that many changes and modifications can be made thereto without departing from the spirit and scope of embodiments of the invention as set forth herein.

What is claimed is:

1. A hydrogel liquid precursor comprising:
   an inorganic mineral; and
   a monomer,
   wherein the inorganic mineral accounts for 15 percent by mass or more of the hydrogel liquid precursor,
   wherein the hydrogel liquid precursor has an initial viscosity of 20 mPa·s or less at 25 degrees C., and
   wherein the hydrogel liquid precursor has a ratio of a two-week viscosity to the initial viscosity of from 0.90 to 1.10, the two-week viscosity representing a viscosity of the hydrogel liquid precursor at 25 degrees C. after being left at 50 degrees C. for two weeks.

2. The hydrogel liquid precursor according to claim 1, wherein the monomer includes an active energy ray polymerizable monomer.

3. The hydrogel liquid precursor according to claim 1, further comprising a phosphonic acid compound.

4. The hydrogel liquid precursor according to claim 3, wherein the phosphonic acid compound is represented by the following Chemical formula 1, Chemical formula 1

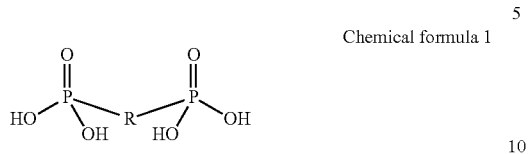

where R represents a substituted or non-substituted divalent substitution group.

5. The hydrogel liquid precursor according to claim 4, wherein R in the Chemical formula 1 includes —($R_1$)C ($R_2$)—, where $R_1$ and $R_2$ each, independently represent substituted or non-substituted alkyl groups.

6. The hydrogel liquid precursor according to claim 4, wherein R in the Chemical formula 1 includes —(OH)C ($CH_3$)—.

7. A method of manufacturing a three-dimensional object, the method comprising:
   manufacturing a hydrogel modeling object using a hydrogel liquid precursor of claim 1.

8. A hydrogel modeling object manufactured by the method of claim 7 and having an 80 percent compressive stress-strain of 1.0 MPa or more.

* * * * *